United States Patent
Cote (10) Patent No.: US 9,044,265 B2
(45) Date of Patent: Jun. 2, 2015

(54) RETRACTABLE SAFETY KNIFE

(75) Inventor: Dana Michael Cote, Boxford, MA (US)

(73) Assignee: Beaver-Visitec International (US), Inc., Lake Forest, IL (US)

(*) Notice: Subject to any disclaimer, the term of this patent is extended or adjusted under 35 U.S.C. 154(b) by 0 days.

(21) Appl. No.: 12/929,016

(22) Filed: Dec. 22, 2010

(65) Prior Publication Data

US 2011/0098734 A1    Apr. 28, 2011

Related U.S. Application Data

(63) Continuation of application No. 12/068,494, filed on Feb. 7, 2008.

(51) Int. Cl.
  *B26B 1/08* (2006.01)
  *A61B 17/32* (2006.01)
  *A61B 17/3211* (2006.01)
  *A61F 9/013* (2006.01)

(52) U.S. Cl.
  CPC ... *A61B 17/3211* (2013.01); *A61B 2017/32113* (2013.01); *A61F 9/0133* (2013.01)

(58) Field of Classification Search
  USPC .............. 30/1.5, 2, 27, 62–67, 151–164, 329, 30/330, 335–340, 342, 344, 510; 606/167
  See application file for complete search history.

(56) References Cited

U.S. PATENT DOCUMENTS

| | | | |
|---|---|---|---|
| 1,195,169 A | 8/1916 | Adcock | |
| 1,914,153 A | 6/1933 | Ogden | |
| 2,207,296 A * | 7/1940 | Lee | 15/433 |
| 2,304,332 A | 12/1942 | Bodkin | |
| 2,512,237 A | 6/1950 | Mravik | |
| 2,885,779 A | 5/1959 | Newkirk | |
| 2,885,780 A | 5/1959 | Campbell | |
| 2,896,317 A | 7/1959 | Vaive | |
| 3,176,395 A * | 4/1965 | Warner et al. | 30/154 |
| 3,192,624 A * | 7/1965 | Gringer | 30/162 |
| 3,383,763 A | 5/1968 | Strandfors | |
| 3,518,758 A | 7/1970 | Bennett | |
| 3,706,106 A | 12/1972 | Leopoldi | |
| 3,905,101 A | 9/1975 | Shepherd | |
| 3,906,626 A | 9/1975 | Riuli | |

(Continued)

FOREIGN PATENT DOCUMENTS

| | | |
|---|---|---|
| DE | 3722899 | 1/1989 |
| EP | 0 162 170 | 11/1985 |

(Continued)

OTHER PUBLICATIONS

Surgistar Website, "881861 Slit 1.8mm Safety Knife Angled", Downloaded Apr. 28, 2011, product p. 1, product enlargement p. 2, www.surgistar.com/product_detail.php?i=839.

(Continued)

*Primary Examiner* — Hwei C Payer
(74) *Attorney, Agent, or Firm* — Roylance, Abrams, Berdo & Goodman, L.L.P.

(57) ABSTRACT

A retractable safety knife has a hollow handle with an opening at an end thereof, a pusher that is movably disposed within the handle and is operable by a user, and a blade that is connected with an end of the pusher. When the pusher moves from a blade-retracted position to a blade-extended position, the blade extends outwardly from the handle opening and rotates from a nested position to an extended position.

18 Claims, 7 Drawing Sheets

(56) References Cited

U.S. PATENT DOCUMENTS

| | | | |
|---|---|---|---|
| 3,943,627 A | 3/1976 | Stanley, Jr. | |
| 3,967,377 A | 7/1976 | Wells | |
| 4,091,537 A | 5/1978 | Stevenson, Jr. | |
| 4,096,629 A | 6/1978 | Levine | |
| 4,265,017 A | 5/1981 | Collins | |
| 4,356,631 A | 11/1982 | Guth | |
| 4,375,218 A | 3/1983 | DiGeronimo | |
| 4,393,587 A | 7/1983 | Kloosterman | |
| 4,414,974 A | 11/1983 | Dotson et al. | |
| 4,491,132 A | 1/1985 | Aikins | |
| 4,499,898 A | 2/1985 | Knepshield et al. | |
| 4,500,220 A | 2/1985 | Hashimoto | |
| 4,516,575 A | 5/1985 | Gerhard et al. | |
| 4,523,379 A | 6/1985 | Osterhout et al. | |
| 4,538,356 A | 9/1985 | Knepshield et al. | |
| 4,576,164 A | 3/1986 | Richeson | |
| D283,544 S | 4/1986 | Schmidt et al. | |
| 4,630,378 A | 12/1986 | Kulp et al. | |
| 4,660,287 A | 4/1987 | Decker | |
| 4,662,075 A | 5/1987 | Mastel et al. | |
| 4,719,915 A | 1/1988 | Porat et al. | |
| 4,735,202 A | 4/1988 | Williams | |
| 4,757,612 A | 7/1988 | Peyrot | |
| 4,815,218 A | 3/1989 | Gordy | |
| 4,823,457 A | 4/1989 | Prochaska | |
| 4,825,545 A | 5/1989 | Chase et al. | |
| 4,826,339 A | 5/1989 | Sasaki | |
| 4,910,821 A | 3/1990 | Kieferle | |
| 4,958,625 A | 9/1990 | Bates et al. | |
| 4,985,034 A | 1/1991 | Lipton | |
| 5,015,252 A | 5/1991 | Jones | |
| 5,035,703 A | 7/1991 | Baskas | |
| 5,071,426 A | 12/1991 | Dolgin et al. | |
| 5,139,507 A | 8/1992 | Dolgin et al. | |
| 5,203,865 A | 4/1993 | Siepser | |
| 5,207,696 A | 5/1993 | Matwijcow | |
| 5,222,951 A | 6/1993 | Abidin et al. | |
| 5,250,063 A | 10/1993 | Abidin et al. | |
| 5,254,128 A | 10/1993 | Mesa | |
| 5,275,606 A | 1/1994 | Abidin et al. | |
| 5,292,329 A | 3/1994 | Werner | |
| 5,299,357 A | 4/1994 | Wonderley et al. | |
| 5,309,641 A | 5/1994 | Wonderley et al. | |
| 5,312,429 A | 5/1994 | Noack | |
| 5,330,492 A | 7/1994 | Haugen | |
| 5,330,493 A | 7/1994 | Haining | |
| 5,330,494 A | 7/1994 | Vander Westhuizen et al. | |
| 5,336,235 A | 8/1994 | Myers | |
| 5,342,379 A | 8/1994 | Volinsky | |
| 5,344,424 A * | 9/1994 | Roberts et al. | 606/167 |
| 5,352,220 A | 10/1994 | Abidin et al. | |
| 5,361,902 A | 11/1994 | Abidin et al. | |
| 5,370,654 A | 12/1994 | Abidin et al. | |
| 5,411,512 A | 5/1995 | Abidin et al. | |
| 5,417,704 A | 5/1995 | Wonderley | |
| 5,431,672 A | 7/1995 | Cote et al. | |
| 5,433,321 A | 7/1995 | Abidin et al. | |
| 5,475,925 A | 12/1995 | Newman et al. | |
| 5,496,340 A | 3/1996 | Abidin et al. | |
| 5,507,762 A | 4/1996 | Abidin et al. | |
| 5,528,811 A | 6/1996 | Abidin et al. | |
| 5,545,175 A | 8/1996 | Abidin et al. | |
| 5,569,281 A | 10/1996 | Abidin et al. | |
| 5,571,127 A * | 11/1996 | DeCampli | 606/167 |
| 5,577,850 A * | 11/1996 | Mishima | 401/83 |
| 5,599,351 A * | 2/1997 | Haber et al. | 606/167 |
| 5,601,572 A | 2/1997 | Middleman et al. | |
| 5,613,300 A * | 3/1997 | Schmidt | 30/2 |
| 5,620,454 A | 4/1997 | Pierce et al. | |
| 5,662,221 A | 9/1997 | Abidin et al. | |
| 5,662,669 A | 9/1997 | Abidin et al. | |
| 5,664,668 A | 9/1997 | Zainal et al. | |
| 5,665,099 A | 9/1997 | Pilo et al. | |
| D386,526 S * | 11/1997 | Ito | D19/53 |
| 5,683,407 A | 11/1997 | Jolly et al. | |
| 5,727,682 A | 3/1998 | Abidin et al. | |
| 5,741,289 A | 4/1998 | Jolly et al. | |
| 5,749,886 A | 5/1998 | Abidin et al. | |
| 5,752,968 A | 5/1998 | Jolly et al. | |
| 5,779,724 A | 7/1998 | Werner | |
| 5,792,162 A | 8/1998 | Jolly et al. | |
| 5,827,309 A | 10/1998 | Jolly et al. | |
| 5,908,432 A * | 6/1999 | Pan | 606/167 |
| 5,919,201 A | 7/1999 | Carter et al. | |
| 5,924,206 A | 7/1999 | Cote et al. | |
| 5,938,676 A | 8/1999 | Cohn et al. | |
| D421,303 S | 2/2000 | Cote et al. | |
| 6,048,354 A * | 4/2000 | Lawrence | 606/185 |
| 6,065,889 A | 5/2000 | Maruyama et al. | |
| 6,079,106 A | 6/2000 | Vallotton | |
| 6,089,775 A | 7/2000 | Yokouchi | |
| 6,112,420 A | 9/2000 | Schickerling | |
| 6,261,265 B1 | 7/2001 | Mosseri | |
| 6,391,041 B1 | 5/2002 | Edens | |
| D463,555 S | 9/2002 | Etter et al. | |
| D465,279 S | 11/2002 | Etter et al. | |
| D466,214 S | 11/2002 | Otsuka | |
| 6,503,262 B1 | 1/2003 | Edens | |
| D470,938 S | 2/2003 | Howell et al. | |
| 6,569,175 B1 | 5/2003 | Robinson | |
| 6,626,925 B2 | 9/2003 | Newman et al. | |
| 6,629,985 B1 | 10/2003 | Kiehne | |
| D496,730 S | 9/2004 | Morawski et al. | |
| 6,854,187 B2 | 2/2005 | Huan | |
| D504,513 S | 4/2005 | Morawski et al. | |
| 6,884,240 B1 | 4/2005 | Dykes | |
| 6,948,250 B1 * | 9/2005 | Caiafa et al. | 30/162 |
| 7,022,128 B2 | 4/2006 | Morawski et al. | |
| 7,055,248 B2 | 6/2006 | Cote | |
| 7,121,005 B2 | 10/2006 | Hughes | |
| D533,944 S | 12/2006 | Sullivan et al. | |
| 7,150,754 B2 | 12/2006 | Ziemer | |
| D537,528 S | 2/2007 | Christensen et al. | |
| 7,185,435 B1 | 3/2007 | Tseng | |
| D571,010 S | 6/2008 | Cote | |
| 7,387,637 B2 * | 6/2008 | Morawski et al. | 606/167 |
| 7,520,059 B2 | 4/2009 | Ranieri et al. | |
| 7,905,894 B2 * | 3/2011 | Morawski et al. | 606/167 |
| D642,682 S | 8/2011 | Chaudhary et al. | |
| 8,114,103 B2 * | 2/2012 | Rasco | 606/167 |
| 8,256,331 B2 * | 9/2012 | Auchter et al. | 83/13 |
| 8,464,430 B2 * | 6/2013 | Cote | 30/162 |
| 2002/0065532 A1 | 5/2002 | Harrold et al. | |
| 2002/0143352 A1 | 10/2002 | Newman et al. | |
| 2003/0225428 A1 * | 12/2003 | Saito et al. | 606/167 |
| 2004/0215174 A1 | 10/2004 | Morawski et al. | |
| 2005/0015104 A1 | 1/2005 | Morawski et al. | |
| 2005/0119680 A1 | 6/2005 | Dykes | |
| 2005/0138816 A1 | 6/2005 | Ping | |
| 2005/0267502 A1 | 12/2005 | Hochman | |
| 2006/0085019 A1 | 4/2006 | Cote et al. | |
| 2008/0141539 A1 * | 6/2008 | Co | 30/162 |
| 2009/0204136 A1 | 8/2009 | Endo | |

FOREIGN PATENT DOCUMENTS

| | | |
|---|---|---|
| EP | 0 555 196 | 8/1993 |
| EP | 0 653 190 | 5/1995 |
| EP | 0 701 798 | 3/1996 |
| TW | 244896 | 4/1995 |
| WO | WO 93/11916 | 6/1993 |
| WO | WO 93/21837 | 11/1993 |
| WO | WO 97/37599 | 10/1997 |
| WO | WO 01/05312 A1 | 1/2001 |
| WO | WO 03/099145 | 12/2003 |
| WO | WO 2008/029566 | 3/2008 |

OTHER PUBLICATIONS

Surgistar Advertisement, "Self-Defense / Safety Doesn't Happen by Accident / Introducing the Safety Knife Series From Surgistar", Eurotimes, Feb. 2011, cover page and p. 6, vol. 16, Issue 2.

(56) References Cited

OTHER PUBLICATIONS

Surgistar Brochure, "Self-Defense / Safety Doesn't Happen by Accident / Introducing the Safety Knife Series From Surgistar", Copyright 2010, pp. 1 and 2.

Oasis Medical Inc., "Oasis Priemier Shield Safety Scalpels," Oasis Product Catalog, 2006, Glendora California.

Carroll Design Web Page, Captured Jan. 24, 2001, http://web.archive.org/web/20010124202600/http://www.carrolldesign.com/mentor_orca.htm.

* cited by examiner

FIG. 13B

RETRACTABLE SAFETY KNIFE

CROSS-REFERENCE TO RELATED APPLICATION

This application is a continuation of U.S. Non-Provisional patent application Ser. No. 12/068,494, filed Feb. 7, 2008 in the U.S. Patent and Trademark Office, now U.S. Pat. No. 8,464,430 the disclosure of which is incorporated herein by reference in its entirety.

BACKGROUND OF THE INVENTION

1. Field of the Invention

The present invention relates to a retractable safety knife, and more particularly, to a apparatus and method for a surgical retractable safety knife; for both ophthalmic and non-ophthalmic applications, in which a blade is retracted within a handle of the knife.

2. Description of the Related Art

In various surgical procedures, the surgeon typically has to make an incision in the patient to remove unwanted tissue, repair damaged tissue, or implant a device to improve the patient's well being. In certain cases, all three of these activities, or a combination thereof, must be done in a single procedure. For example, in cataract surgery, the surgeon removes a natural, ocular lens that has been clouded by a cataract and replaces it with an artificial lens that will improve the patient's eyesight. To perform this procedure, an incision is made in the cornea using a scalpel. This provides the surgeon with access to the patient's natural lens. The clouded lens is cut loose and removed. There are a number of different procedures used to remove a patient's lens. Two of the more common techniques are known as extracapsular surgery and phacoemulsification.

In extracapsular surgery, the surgeon removes the lens leaving behind the back half of the capsule. In phacoemulsification, the surgeon fragments the lens by ultrasonic vibrations and the lens is simultaneously irrigated and aspirated. After the lens is removed, the surgeon inserts an artificial lens, known as an intraocular lens (IOL), into the eye either behind or in front of the iris. Two C-shaped arms connected to the IOL eventually become scarred into the side of the eye and hold the IOL firmly in place.

In another type of ophthalmic procedure known as the Implantable Contact Lens procedure (ICL), the surgeon makes an incision in the patient's eye and implants a contact lens in the eye in front of the existing lens but behind the iris. This corrects the patient's vision so that he or she can see clearly without the need for external contact lenses or eyeglasses.

Typically a nurse or other surgical assistant manages the devices used during such delicate surgeries. For example, the assistant ensures that the appropriate sterile devices are available in the operating suite for the particular procedure that is to be performed. With respect to scalpels, the nurse often hands the scalpel to the surgeon in a predetermined orientation so that the surgeon can grip the scalpel's handle without taking his or her eyes away from the patient. This also minimizes the possibility that the surgeon may be cut with the blade on the scalpel. After the surgeon completes the incision, the scalpel is handed back to the assistant for proper disposal or sterilization. While the procedure is being performed, this requires the assistant to place the used scalpel on a particular tray that will be removed after the procedure is completed. The devices on the tray are then disposed of or are sterilized for reuse.

If all appropriate protocols are followed, no hospital personnel will be cut by used or unused scalpel blades. Unfortunately, accidental cuts of hospital personnel do occur for a variety of reasons. For example, because the surgeon and assistant are concentrating on the patient and the procedure being performed on the patient, they may not pay close attention to the scalpels. The assistant may put the used scalpels in an inappropriate location or, even if the used scalpels are placed on the proper tray, the blade may be exposed to the operating suite personnel. In these situations, the operating suite personnel may inadvertently come into contact with the blade as they move around the patient during the procedure and be cut or nicked by an exposed blade.

Other hospital personnel may also come into contact with such blades and may also be cut or nicked. Usually, used blades are disposed of in an appropriate sharps container that allows used needles and blades to be inserted into the container but prevents access by hospital personnel to the sharp end of a needle or the sharp cutting surface of the blade. However, during cleanup of the operating suite, the used blades may be exposed prior to their placement in the appropriate sharps container. If hospital personnel are not paying close attention to their activities, or if the exposed blades are hidden from view because they are buried in a pile of other devices or hospital linen, these hospital personnel may come into contact with the sharp cutting surface of the blade and be cut or nicked.

Cuts and nicks from blades are uncomfortable and distracting at best. In addition, such cuts and nicks from used blades may result in blood or body fluid exposure which can result in the spread of infectious diseases between the patient and hospital personnel. Concern over this situation has become especially acute in recent years because of such diseases as acquired immunodeficiency syndrome, i.e. AIDS, and hepatitis. These diseases may be transmitted from an infected person to another person by the transmission of body fluids, typically blood.

Further, the blade of the scalpel must be protected from accidental damage prior to intended use.

In view of the need for a scalpel that can at least minimize the chances of accidental cuts or nicks, while also protecting the cutting edge of the blade, numerous scalpels have been designed. These designs typically take the form of a scalpel having a guard that shields the sharp cutting surface of the blade from undesired contact with hospital personnel and surrounding surfaces. The guard in these devices can be extended to a position shielding the blade or retracted exposing the blade for use. Alternatively, the scalpel may be designed to allow the blade to move into or out of the scalpel handle, to either shield or expose the sharp cutting surface.

These designs, however, may require attention by the user to shield or expose the blade. Additionally, the guard (even when transparent) may visually distort the handle outline when retracted. Any design that allows the blade to move, for retraction or extension purposes, also introduces design issues regarding exact blade positioning and rigidity during use. Such issues also apply in cases in which the user is required to hold the retracted guard as a grip.

SUMMARY OF THE INVENTION

Accordingly, it is an aspect of embodiments of the present invention to provide a safety knife that protects people from accidental cuts and protects the blade from accidental damage, as well as affords a clear view of the blade during use, and affords good tactile feedback to a user.

The foregoing and/or other aspects of embodiments of the present invention are achieved by providing an apparatus, including a hollow handle having an opening at an end thereof, a pusher movably disposed within the handle and operable by a user, and a blade connected with an end of the pusher. When the pusher moves from a blade-retracted position to a blade-extended position, the blade extends outwardly from the handle opening and rotates from a nested position to an extended position.

The foregoing and/or other aspects of embodiments of the present invention are also achieved by providing an apparatus, including a hollow handle having an opening at an end thereof, and a tilt track; a pusher movably disposed within the handle and operable by a user, the pusher comprising a main portion connected with a tilt beam, the tilt beam having a tilt pin disposed thereon, the tilt pin engaging the tilt track; and a blade connected with an end of the tilt beam. The tilt track defines a guide path for the tilt pin during extension and retraction of the blade, to deflect the tilt beam, thereby rotating the blade relative to the handle and translating the blade relative to the handle.

The foregoing and/or other aspects of embodiments of the present invention are also achieved by providing an apparatus, including a hollow handle having an opening at an end thereof, and a tilt track; a pusher movably disposed within the handle and operable by a user, the pusher comprising a main portion connected with a tilt beam, the tilt beam having a tilt pin disposed thereon, the tilt pin engaging the tilt track; and a blade connected with an end of the tilt beam. When the pusher moves from a blade-extended position to a blade-retracted position, the tilt pin moves in the slot, deflecting the tilt beam, and the blade rotates relative to the handle, from an extended position to a nested position, and retracts through the handle opening; and/or when the pusher moves from the blade-retracted position to the blade-extended position, the tilt pin moves in the slot, deflecting the tilt beam, and the blade extends through the handle opening and rotates from the nested position to the extended position.

The foregoing and/or other aspects of embodiments of the present invention are also achieved by providing an apparatus, including a substantially cylindrical handle defining a chamber therein and having at least one slot extending along a longitudinal axis accessing the chamber, the chamber being open at a distal end of the handle, the chamber having a tilt track disposed therein defining a guide path; a pusher movably disposed within the chamber and having a control mechanism protruding through the longitudinal handle slot, the pusher comprising a main portion connected with a tilt beam, the tilt beam having a tilt pin disposed thereon, the tilt pin engaging the tilt track and being guided along the guide path; and a blade connected with an end of the tilt beam. Moving the pusher control mechanism between opposing ends of the longitudinal handle slot translates the main portion of the pusher, moves the tilt pin along the guide path, deflects the tilt beam, and translates and rotates the blade between a nested position, retracted within the chamber, and an extended position external to the chamber, via the distal opening of the handle.

The foregoing and/or other aspects of embodiments of the present invention are also achieved by providing a method for shielding and exposing a blade in a surgical instrument, comprising at least one of rotating the blade relative to a handle of the surgical instrument, from an extended position to a nested position, and retracting the blade through a handle opening; and extending the blade through the handle opening and rotating from the nested position to the extended position.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which:

FIGS. 5A and B illustrate top and bottom views of a base of the safety knife of FIG. 3;

FIGS. 6A and B illustrate top and bottom views of a cover of the safety knife of FIG. 3;

DETAILED DESCRIPTION OF EMBODIMENTS OF THE PRESENT INVENTION

Reference will now be made in detail to embodiments of the present invention, examples of which are illustrated in the accompanying drawings, wherein like reference numerals refer to the like elements throughout. The embodiments described exemplify the present invention by referring to the drawing figures.

Figure 1:
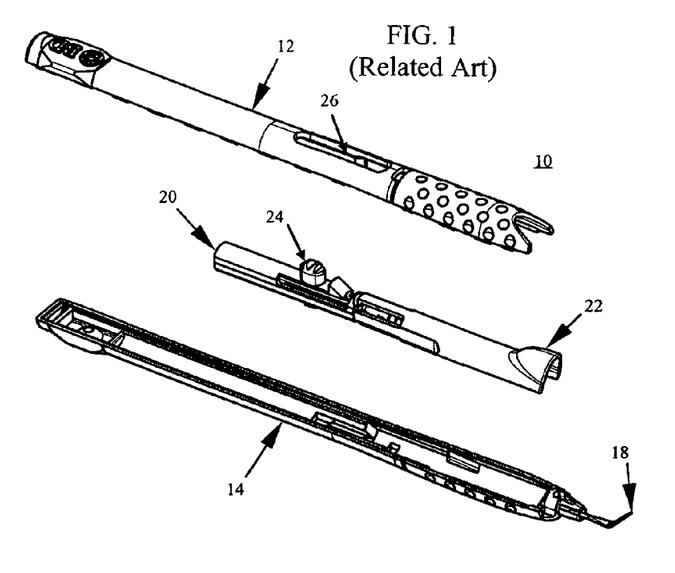
FIG. 1 illustrates an exploded view of a related art safety knife with a retractable guard.
Figure 2A:
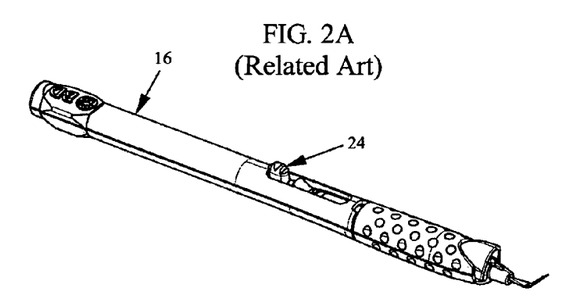
FIGS. 2A and B respectively illustrate the safety knife of FIG. 1 with the guard in retracted and extended positions.
Figure 2B:
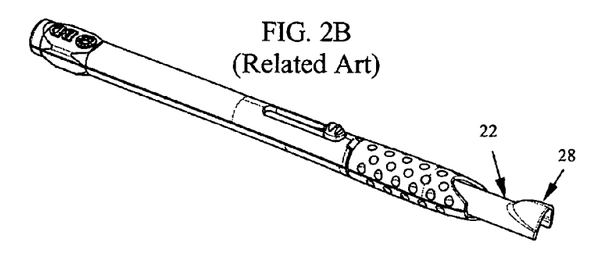

Solutions to the above-described related art problems can be found in commonly-assigned U.S. Pat. No. 7,022,128 and U.S. patent application Ser. Nos. 10/828,501, now U.S. Pat. No. 7,387,637, and 11/252,575, now U.S. Pat. No. 7,909,840, all of which are hereby incorporated by reference in their entirety. A device in accordance with the last-mentioned application is shown in FIGS. 1, 2A, and 2B. FIG. 1 illustrates an exploded view of a safety knife with a retractable guard, and FIGS. 2A and B respectively illustrate the safety knife of FIG. 1 with the guard in retracted and extended positions.

As shown in FIGS. 1, 2A, and 2B, the safety knife 10 includes a cover 12 and a base 14, which together form a hollow handle 16. The base 14 includes a blade 18, which in the illustrated embodiment is a bent blade. A pusher 20 is disposed within the handle 16, and includes a shield or guard 22, which selectively covers the blade 18, and a button 24, which extends through slot 26 of cover 12. As shown in FIG. 2B, the guard 22 includes an enlarged distal end 28, due to the angled nature of the bent blade 18. When a user slides button 24 to a rear of slot 26, guard 22 is retracted, exposing blade 18 for use. And when the user slides button 24 to a front of slot 26, guard 22 slides forward so that enlarged distal end 28 covers the blade 18, thereby protecting a user from an accidental injury, and protecting the blade 18.

While the safety knife 10 accomplishes these goals, in the extended position, it may be possible to deflect the guard 22 into the blade. Further, while the enlarged distal end 28 may be made of a transparent material, the curved surface may distort a surgeon's view of the blade 18 (see, e.g., FIG. 13B).

Figure 3:
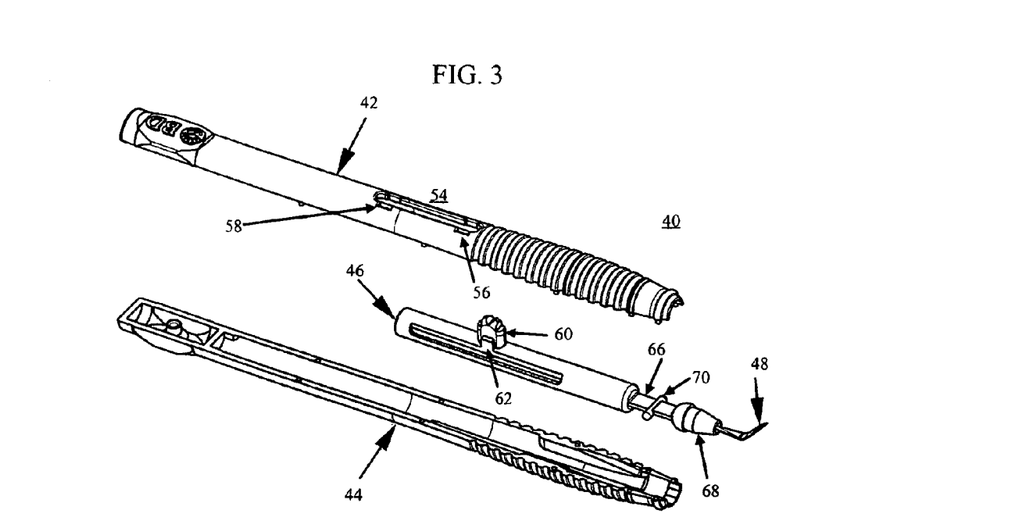
FIG. 3 illustrates an exploded view of a retractable safety knife according to a first embodiment of the present invention.
Figure 4A:
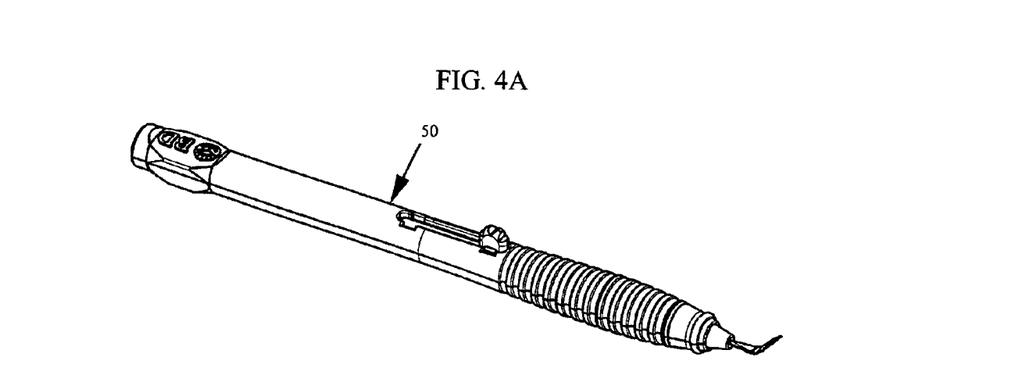
FIGS. 4A and B respectively illustrate the retractable safety knife of FIG. 3 in blade-extended and blade-retracted positions.
Figure 4B:
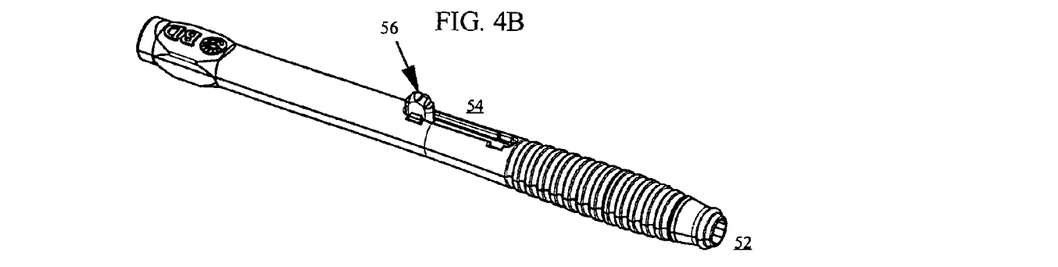

FIG. 3 illustrates an exploded view of a retractable safety knife according to an embodiment of the present invention. FIGS. 4A and B respectively illustrate the retractable safety knife of FIG. 3 in blade-extended and blade-retracted positions. As shown in FIGS. 3, 4A, and 4B, retractable safety knife 40 includes a cover 42, a base 44, a pusher 46, and a blade 48. According to one embodiment, the cover 42 and the base 44 are ultrasonically welded together to form a handle 50. Further, according to one embodiment, the retractable safety knife 40 is distributed as a product with the pusher 46 and blade 48 in the retracted or safe position.

Figures 5A, 5B:
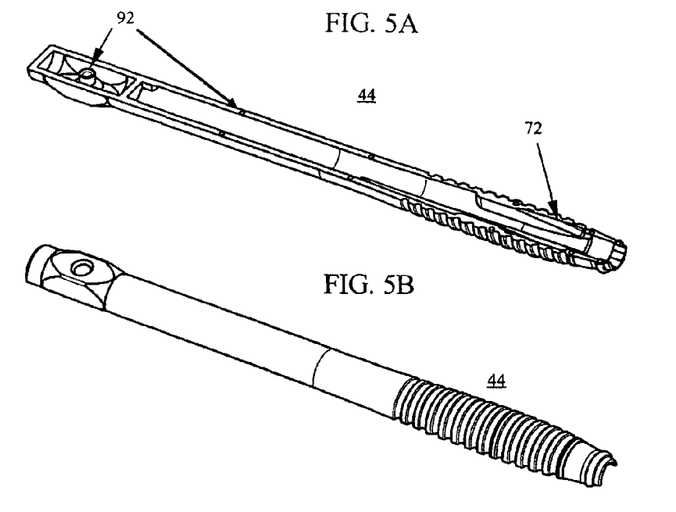

FIGS. 5A and B illustrate top and bottom views of base 44. Similarly, FIGS. 6A and B illustrate top and bottom views of cover 42. As shown in FIGS. 5A, 5B, 6A, and 6B, according to one embodiment, cover 42 has a plurality of alignment pins 90 and base 44 has a corresponding plurality of alignment holes or alignment bushings 92. During assembly, the alignment pins 90 are inserted into the alignment bushings 92 to align the cover 42 and the base 44 to form the handle 50. According to another embodiment, alignment pins 90 are disposed on base 44, and alignment bushings 92 are disposed on cover 42. According to yet another embodiment, alignment pins 90 and alignment bushings 92 are disposed on base 44, and corresponding alignment bushings 92 and alignment pins 90 are disposed on cover 42.

Referring back to FIGS. 3, 4A, and 4B, the handle 50 is substantially cylindrical, and is hollow to define a chamber therein. Additionally, as best shown in FIG. 4B, handle 50 has an opening 52 at a distal end thereof, and a slot or opening 54 that extends along a longitudinal axis of the handle 50 and accesses the chamber. As shown in FIG. 4B, according to one embodiment, the opening 52 is substantially circular. Slot 54 has detents 56 and 58, corresponding, respectively, to the blade-extended and blade-retracted positions. According to one embodiment, detents 56 and 58 are each formed as respective pairs disposed on opposing transverse sides of the slot 54 (see, e.g., FIG. 13B).

The pusher 46 is disposed substantially within the handle 50 to slide within the chamber, and has a button 60 disposed on a top of a main portion or beam 64 thereof, corresponding with the slot 54. Button 60 has a projection or button stop 62 disposed on a side thereof. According to one embodiment, projection 62 is one of a pair of projections disposed on opposing sides of button 60. In use, the projection 62 selectively engages the detents 56 and 58 to secure the pusher 46 (and the blade 48, as will be discussed in greater detail below) in the blade-retracted and blade-extended positions. According to one embodiment, as shown, for example, in FIG. 7A, the pusher 46 has an enclosed slot 63, and the projection 62 is designed to ease disengagement with the detents 56 or 58. In operation, once the projection 62 is engaged with the one of the detents 56 or 58, the user depresses the button 60 (pushing inwardly with respect to the handle 50) to disengage from the current detent. Then, the user slides the button 60 to advance it toward the target detent, and there is an audible click, as the projection 62 snaps into the target detent, to confirm positioning therein. According to another embodiment, the user moves the button 60 sideways to disengage the projection from a detent, either 56 or 58 and slides the button 60 to advance it toward the target detent.

According to an alternative embodiment (not shown), the positioning of the detents and the projection is reversed, i.e., the slot 54 has projections corresponding, respectively, to the blade-extended and blade-retracted positions, and the button has a detent that selectively engages the projections.

Figures 7A, 7B, 8A:
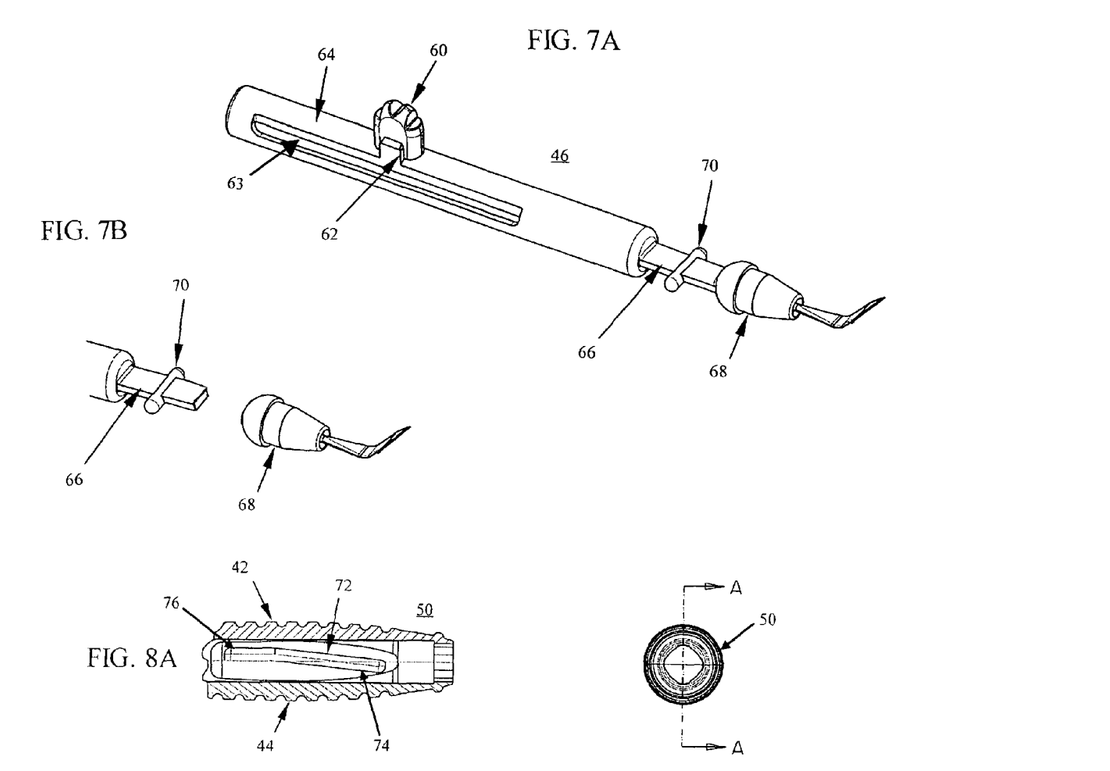
FIG. 7A illustrates a pusher of the safety knife of FIG. 3.
FIG. 7B illustrates a pusher according to another embodiment of the present invention.
FIG. 8A illustrates cutaway and end views of an end of a handle of the safety knife of FIG. 3.

FIG. 7A illustrates the pusher 46 of the safety knife 40. As shown in FIGS. 3 and 7A, a tilt beam 66 made of plastic, metal, or other rigid, but resilient material extends from an end of the main portion 64 of the pusher 46, and the blade 48 is connected with an end of the tilt beam 66. The tilt beam has a tilt pin 70 disposed thereon. According to one embodiment, the blade is connected with a first end of a head 68, and a second end of the head, opposite to the first end, is connected with the tilt beam 66. The blade 48 can be connected with the head 68 in any desired manner, e.g., by being glued, press fitted, snapped, screwed, and/or molded to the head 68. According to one embodiment, shown, for example, in FIG. 7B, the head 68 is detachable from the tilt beam 66. In such an embodiment, the head 68 can be connected with the tilt beam 66 by being glued, press fitted, snapped, and/or screwed to the tilt beam 66.

Figure 8B:
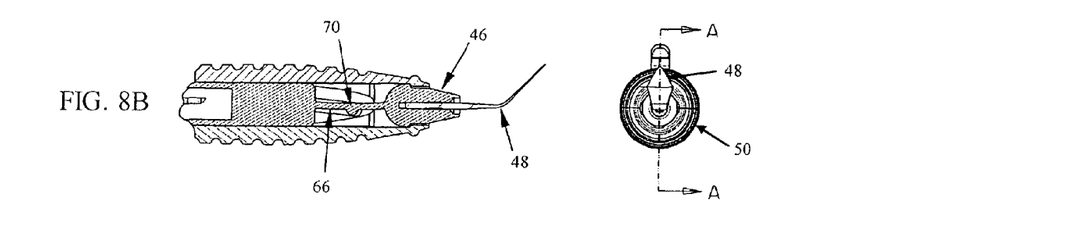
FIG. 8B illustrates cutaway and end views of the pusher, a blade, and the end of the handle of the safety knife of FIG. 3 in the blade-extended and extended positions.
Figure 8C:
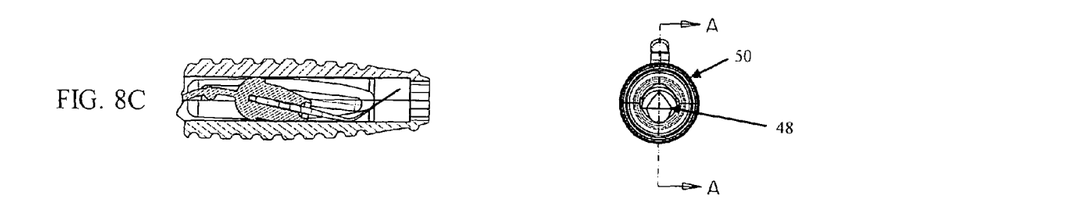
FIG. 8C illustrates cutaway and end views of the pusher, the blade, and the end of the handle of the safety knife of FIG. 3 in the blade-retracted and nested positions.
Figure 9A:
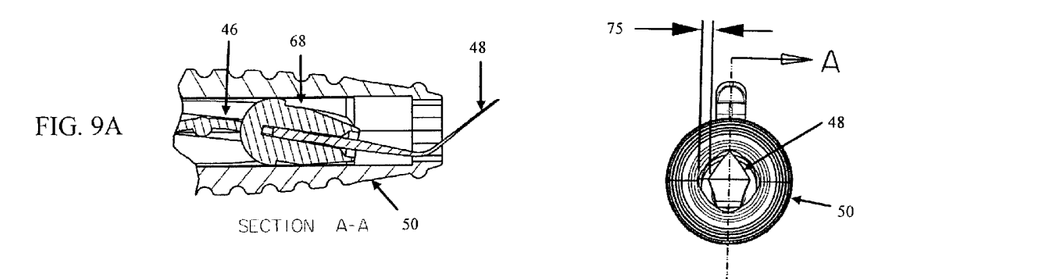
FIG. 9A illustrates enlarged cutaway and end views of the pusher, the blade, and the end of the handle of the retractable safety knife of FIG. 3 between the blade-extended/extended positions and blade-retracted/nested positions.

FIG. 8A illustrates cutaway and end views of an end of the handle 50. FIG. 8B illustrates cutaway and end views of the pusher 46, the blade 48, and the end of the handle 50 in the blade-extended and extended positions. FIG. 8C illustrates cutaway and end views of the pusher 46, the blade 48, and the end of the handle 50 in the blade-retracted and nested positions. FIG. 9A illustrates enlarged cutaway and end views of the pusher 46, the blade 48, and the end of the handle 50 between the blade-extended/extended positions and blade-retracted/nested positions. And FIG. 9B illustrates enlarged cutaway and end views of the pusher 46, the blade 48, and the end of the handle 50 in the blade-retracted and nested positions.

Figures 6A, 6B:
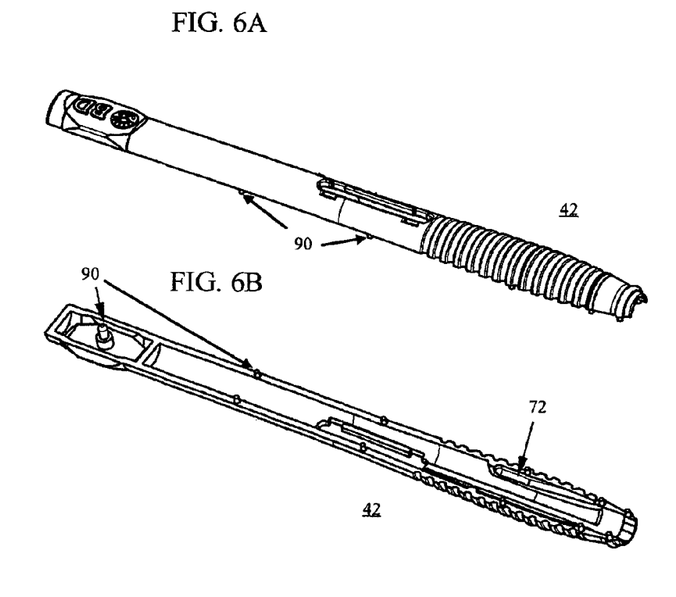

As shown in FIGS. 5A, 6B, and 8A, the handle 50 includes a tilt track 72, which may alternately be referred to as a cam track or tilt slot. According to one embodiment, respective portions of the tilt track 72 are molded in the base 44 and cover 42 during manufacture thereof. According to another embodiment, respective portions of the tilt track 72 are milled in the base 44 and cover 42 during manufacture thereof.

The tilt track 72 defines an inclined (i.e., with respect to the handle axis) guide path for the tilt pin 70. When the pusher 46 is assembled within the chamber of the handle 50, the tilt pin 70 is engaged with tilt track 72. According to one embodiment, the handle 50 has a pair of tilt tracks 72 on opposing sides of the chamber, to guide opposing ends of the tilt pin 70. As shown in FIGS. 8B and 8C, as the pusher 46 is retracted by a user, the tilt pin 70 is forced upward by riding in the tilt track 72. When the tilt pin 70 is forced up the tilt beam 66 is deflected, that is, its shape is changed, such as by deformation (preferably elastic deformation) of the tilt beam 66, as shown in FIGS. 8B and 8C. This causes the head 68 and blade 48 to rotate down. In other words, as the main portion 64 of the pusher 46 moves between the blade-extended and blade-retracted positions, the tilt pin travels in the tilt track 72, deflecting the tilt beam 66, rotating the blade 48 from the extended position to a nested position, and retracting the blade 48 within the handle 50. Conversely, as the main portion 64 of the pusher 46 moves between the blade retracted and blade-extended positions, the tilt pin travels in the tilt track 72, again deflecting (i.e., changing the shape of) the tilt beam 66, extending the blade 48 from the handle 50, and rotating the blade 48 from the nested position to the extended position.

Figure 9B:
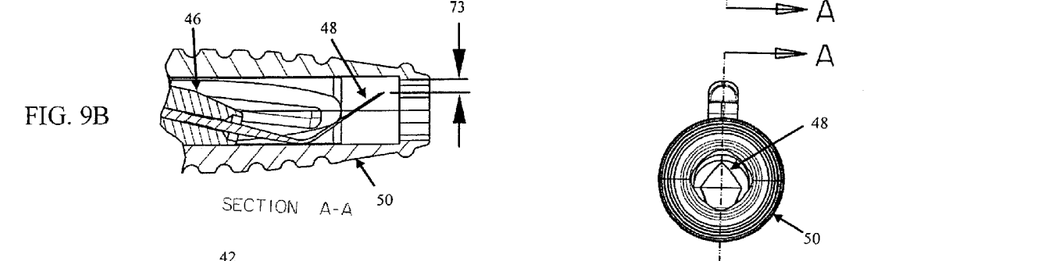
FIG. 9B illustrates enlarged cutaway and end views of the pusher, the blade, and the end of the handle of the retractable safety knife of FIG. 3 in the blade-retracted and nested positions.

FIGS. 9A and 9B respectively show the head 68 and the blade 48 in the nested position between the blade-extended and blade-retracted positions, and in the blade-retracted/nested positions.

Referring back to FIG. 8A, the guide path of tilt track 72 preferably includes a first guide path portion 74 and a second guide path portion 76. The first guide path portion 74 is inclined at an angle of about 5-10° with respect to the substantially linear travel path of the main portion 64 of the pusher 46. According to one embodiment, the first guide path portion 74 is inclined at an angle of about 6.24° with respect to the substantially linear travel path of the main portion 64 of the pusher 46. The second guide path portion 76 adjoins the first guide path portion 74 and is substantially parallel to the travel path of the main portion 64. When the tilt pin 70 travels along the first guide path portion 74, the blade 48 rotates with respect to the handle 50 between the nested and extended positions, as well as translates with respect to the handle 50. And when the tilt pin 70 travels along the second guide path portion 76, the blade 48 translates with respect to the handle 50. Thus, moving the pusher 46 substantially linearly within the handle 50, between the blade-extended and blade-retracted positions results in both translational and rotational movement of the blade 48.

The shape of the tilt track 72 (and in the specific case of the embodiment of FIG. 8A, the angle of the first guide path portion 74) dictates how fast and far the head 68 and blade 48 move. Thus, according to the shape of the tilt track 72 of FIG. 8A, the tip of blade 48 dives down towards the handle's 50 centerline during retraction. But it will be appreciated that embodiments of the present invention are not limited to the first and second guide paths 74 and 76 shown in FIG. 8A. For example, in the modified embodiment of FIG. 10, tilt track 72A is curvilinear. When the tilt pin 70 travels along the tilt track 72A, the blade 48 rotates with respect to the handle 50 between the nested and extended positions, as well as translates with respect to the handle 50.

The blade 48 shown, for example, in FIGS. 3-9B, is depicted as being a round stock blade about 3.2 mm in width and having a bend height of about 0.205 inches (about 5.2 mm). These are substantially the same dimensions as the blade 18 that is depicted in FIGS. 1, 2A, and 2B. With the retractable safety knife 40 however, as shown, e.g., in FIGS. 9A and 9B, such a blade achieves a tip clearance 73 of about 0.039 inches and a side clearance 75 of about 0.031 inches when in the nested and blade-retracted/nested positions. Since a guard does not have to be accommodated within the chamber of handle 50, even if an internal diameter handle 50 is the same as that of handle 16, a larger blade can be accommodated within handle 50. In fact, given the above noted clearances with respect to blade 48 and handle 50, a blade approximately 4.0 mm wide, with a bend height increase of 0.02 inches (total of about 0.225 inches) can be accommodated within handle 50. It will be understood that embodiments of the present invention are not limited to the above-described blades, and that differently sized blades may be employed. Additionally, it will be understood that flat stock blades may be employed.

One issue that may generally arise with retractable knives is a looseness of the blade relative to the handle. For the user, this may introduce "play" into the tactile feedback. To combat this and provide a user with good tactile feedback, in the embodiment of the present invention shown in FIG. 8B, a portion of the head 68 has a cylindrical diameter that has minimal clearance with respect to a bore of the chamber of the handle 50. Additionally, as shown in FIGS. 8A and 8B, when the pusher 46 is moved from the blade-retracted position to the blade-extended position, the tilt pin 70 crosses the longitudinal centerline of the handle 50, tensioning the tilt beam 66.

Figures 10, 11A:
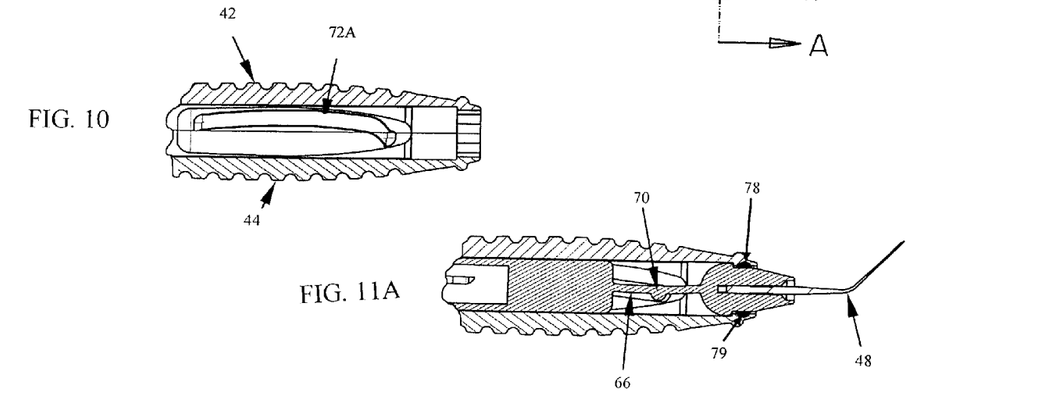
FIG. 10 illustrates a cutaway view of a modified tilt track according to a second embodiment of the present invention.
FIG. 11A illustrates a cutaway view of the handle and the head showing an annular groove and an annular protrusion according to a third embodiment of the present invention.
Figure 11B:
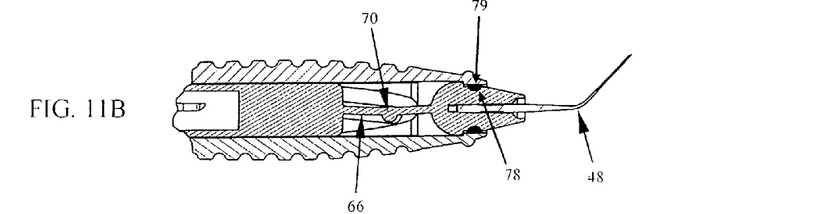
FIG. 11B illustrates a cutaway view of the handle and the head showing an annular groove and an annular protrusion according to another embodiment of the present invention.

Further, according to another embodiment, as shown in FIG. 11A, the handle 50 has an annular groove 78, and the head 68 has an annular protrusion 79. As the blade 48 reaches the extended position, the annular protrusion 79 positively engages the annular groove 78, to stabilize the blade 48 in the extended position. According to another embodiment shown in FIG. 11B, the handle 50 has the annular protrusion 79 and the head 68 has the annular groove 78.

Figure 12A:
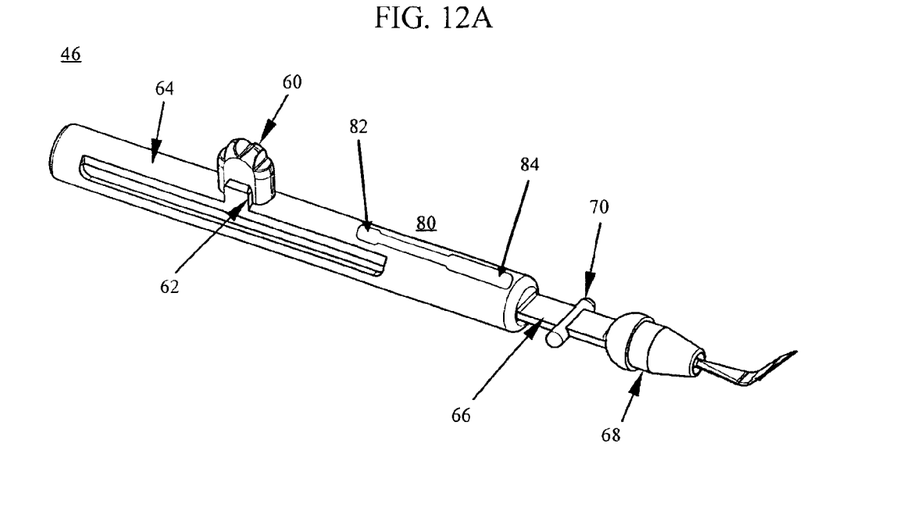
FIGS. 12A-12E illustrate a modified pusher of a safety knife according to a fourth embodiment of the present invention, and an interaction of a slot of the pusher with an alignment pin of the handle.
Figure 12B:
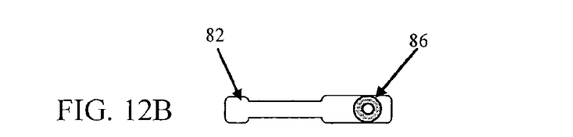
Figure 12C:
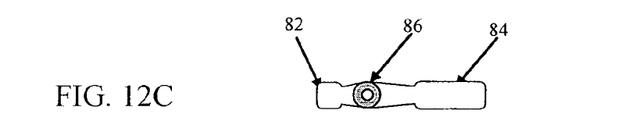
Figure 12D:
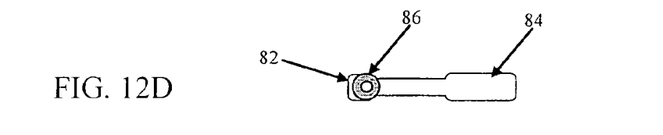
Figure 12E:
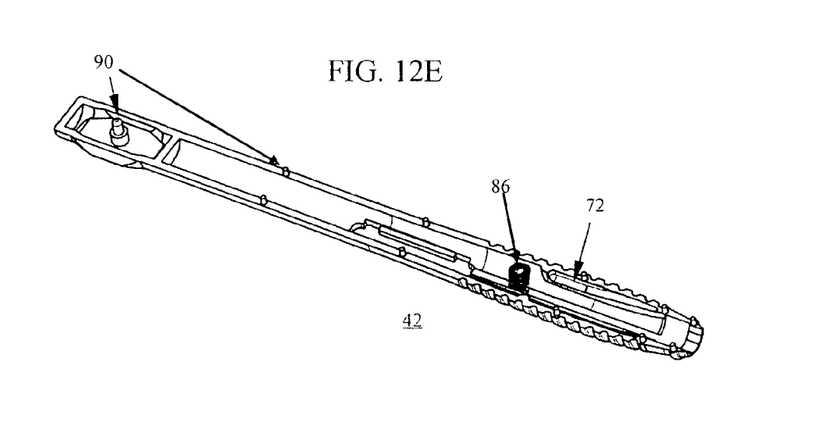

Yet further, according to one embodiment, as shown in FIGS. 12A-12E, the main portion 64 of the pusher 46 has a slot 80 therein extending along a longitudinal axis of the pusher 46, the slot having detents 82 and 84 corresponding to the blade-extended and blade-retracted positions. Additionally, the handle 50 has an inwardly-directed alignment pin 86 (see FIGS. 12B-12E) that is stationary and engages the pusher slot 80 when the safety knife 40 is assembled. Beginning, for example, at the blade-retracted position (FIG. 12B), as the pusher 46 is moved (FIG. 12C) to the blade-extended position (FIG. 12D), the slot 80 moves relative to the alignment pin 86. When the pusher 46 is moved to the blade-extended position though (FIG. 12D), the alignment pin does not fully engage the detent 82, thereby creating a force that urges the pusher 46 toward the blade-extended position. In other words, when the pusher 46 is moved to the blade-extended position, as shown in FIG. 12D, a portion of the alignment pin 86 is still engaged with a constricted portion of the slot 80 disposed between the detents 82 and 84. Because the constricted portion of the slot 80 elastically deforms during relative passage of the alignment pin 86 therethrough (as shown, for example, in FIG. 12C), the portion of the alignment pin 86 still engaged with the constricted portion of the slot 80 when the pusher 46 is moved to the blade-extended position elastically deforms the end of the constricted portion adjacent to the detent 82. Thus, the constricted portion of the slot 80 exerts a force relative to the alignment pin 86 to bias the alignment pin 86 toward the detent 82, and thereby urge the pusher 46 toward the blade-extended position.

Figure 13A:
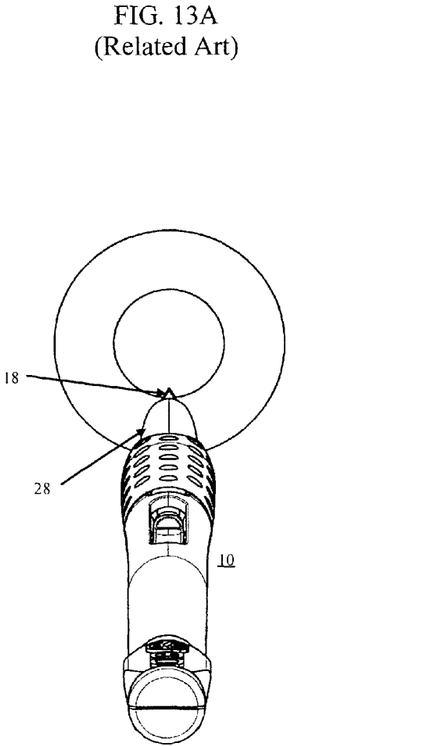
FIGS. 13A and 13B respectively illustrate safety knife 10 of FIG. 1 and retractable safety knife 40 of FIG. 3 in position for a typical clear corneal incision.
Figure 13B:
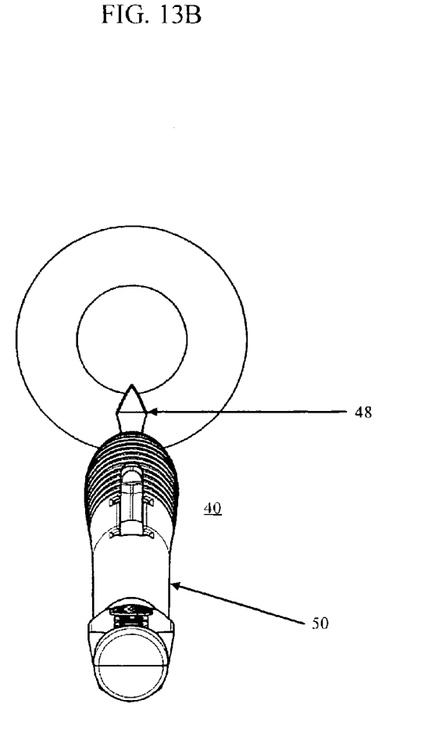

FIGS. 13A and 13B respectively illustrate related art safety knife 10 and retractable safety knife 40 in position for a typical clear corneal incision. As can be seen in FIG. 13B, the configuration of retractable safety knife 40 provides a clear view of the blade 48 for a surgeon, whereas in contrast, the enlarged distal end 28 of related art safety knife 10 (FIG. 13A) may partially obscure the view of blade 18. And, as noted previously, while the enlarged distal end 28 may be made of a transparent material, the curved surface may distort a surgeon's view of the blade 18.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the claims and their equivalents.

The invention claimed is:

1. A surgical knife safety handle, comprising:
    a handle portion having a longitudinal axis, the handle portion comprising a distal end, a proximal end and a housing extending along the longitudinal axis between the distal and proximal ends, the housing having a generally circular opening through which a blade selectively extends, the housing defining a chamber therein and having at least one slot extending along the longitudinal axis accessing the chamber, the housing comprising first engagement structures disposed adjacent to proximal and distal ends of the slot, the first engagement structures being formed as respective pairs disposed on opposing transverse sides of the slot; and
    a pusher for carrying a blade at the distal end of the handle portion, the pusher comprising:
        a main portion having a rounded cross-sectional shape that substantially conforms to the chamber; and
        a user control mechanism extending from within the chamber via the slot for allowing a user to longitudinally move the pusher to selectively expose or at least partially cover the blade, the user control mechanism comprising:
            a button depressible relative to the handle portion, the button having a user contact portion that is narrower than the slot in the transverse direction; and
            a pair of second engagement structures disposed on lateral sides of the button for engagement with the first engagement structures to substantially secure the pusher in a first locking position in which the blade is fully extended and a second locking position in which the blade is at least partially covered, wherein the first and second locking positions define the limits of pusher travel when the button is disposed in the slot, and wherein in the first locking position, a proximal end of the pusher is laterally surrounded by the handle portion;
    wherein a distal-most portion of the slot extends distally beyond the first engagement structures that are disposed adjacent to the distal end of the slot, and a proximal-most portion of the slot extends proximally beyond the first engagement structures that are disposed adjacent to the proximal end of the slot.

2. A surgical knife safety handle according to claim 1, wherein:
    the first engagement structures comprise detent openings; and
    the second engagement structures comprise projections projecting from the lateral sides of the button.

3. A surgical knife safety handle according to claim 1, wherein the pusher, the button, and the second engagement structures are integrally formed as a unitary construction.

4. A surgical knife safety handle according to claim 1, wherein the user contact portion of the button comprises at least one engagement projection for aiding a user's contact with the button.

5. A surgical knife safety handle according to claim 1, wherein the distal end of the handle portion comprises a circumferential textured surface.

6. A surgical knife safety handle according to claim 1, wherein the distal-most portion of the slot corresponds in shape to a distal portion of the button and the proximal-most portion of the slot corresponds in shape to a proximal portion of the button.

7. A surgical knife safety handle, comprising:
    a generally tubular handle portion defining a chamber therein and having a longitudinal slot, the slot accessing the chamber, the handle portion comprising first engagement structures respectively disposed adjacent to proximal and distal ends of the slot on an exterior of the handle portion, the first engagement structures comprising respective pairs of first engagement structures disposed on opposing transverse sides of the slot and defining first and second locking positions; and
    a pusher for longitudinally moving a blade with respect to the handle portion, the pusher comprising:
        a main portion having a rounded cross-sectional shape that substantially conforms to the chamber; and
        a user control mechanism for allowing a user to longitudinally translate at least a portion of the pusher to selectively expose or at least partially cover the blade, the user control mechanism comprising:
            a button fixedly disposed on the main portion of the pusher and extending through the slot, the button being depressible relative to the handle portion and having a user contact portion that is narrower than the slot in a transverse direction of the slot; and
            second engagement structures disposed laterally on the button for engagement with the first engagement structures to substantially secure the pusher in the first locking position in which the blade is fully extended and the second locking position in which the blade is at least partially covered;
    wherein longitudinal translation of the pusher is permitted only between the first and second locking positions when the button is disposed in the slot;
    wherein in the first locking position, a proximal end of the pusher is housed within the handle portion;
    wherein the blade is non-detachably connected to the pusher; and
    wherein a distal-most portion of the slot extends distally beyond the first engagement structures that are disposed adjacent to the distal end of the slot, and a proximal-most portion of the slot extends proximally beyond the first engagement structures that are disposed adjacent to the proximal end of the slot.

8. A surgical knife safety handle according to claim 7, wherein the handle portion comprises a circumferential textured surface disposed at the distal end thereof.

9. A surgical knife safety handle according to claim 7, wherein the button comprises at least one engagement projection for aiding a user's contact with the button.

10. A surgical knife safety handle according to claim 7, wherein:
    the first engagement structures comprise detent openings; and
    the second engagement structures comprise projections projecting from the lateral sides of the button.

11. A surgical knife safety handle according to claim 7, wherein the distal-most portion of the slot corresponds in shape to a distal portion of the button and the proximal-most portion of the slot corresponds in shape to a proximal portion of the button.

12. A surgical knife safety handle, comprising:
a generally tubular handle portion having a first slot through a portion thereof;
a pusher for holding a blade, the pusher comprising:
a main portion having a rounded cross-sectional shape that substantially conforms to the interior of the tubular handle portion, the main portion being longitudinally movable to reciprocate with respect to the handle portion, the main portion including an enclosed second slot; and
a user control mechanism for allowing a user to reciprocate the main portion to selectively expose or at least partially cover the blade, the user control mechanism extending from within the handle portion via the first slot, the user control mechanism comprising a button fixedly disposed on the pusher and button engagement structures laterally disposed on the button, the button being depressible relative to the handle portion and the enclosed second slot; and
pairs of handle portion engagement structures disposed on opposing transverse sides of the first slot adjacent to distal and proximal ends thereof and defining first and second locking positions, wherein the button engagement structures are disposed on an exterior of the handle portion, and are configured to engage the handle portion engagement structures and substantially prevent longitudinal pusher movement during engagement of the engagement structures and permit repeated longitudinal movement of the pusher only between the first and second locking positions when the button is disposed in the first slot;
wherein a lateral surface of a proximal end of the pusher is contained within the handle portion in both of said first and second locking positions; and
wherein the distal-most portion of the first slot extends distally beyond the handle portion engagement structures that are disposed adjacent to the distal end of the first slot, and a proximal-most portion of the first slot extends proximally beyond the handle portion engagement structures that are disposed adjacent to the proximal end of the first slot.

13. A surgical knife safety handle according to claim 12, wherein:
the handle portion engagement structures comprise detent openings; and
the button engagement structures comprise projections projecting from the lateral sides of the button.

14. A surgical knife safety handle according to claim 12, wherein the distal end of the handle portion comprises a circumferential textured surface.

15. A surgical knife safety handle according to claim 12, wherein at least a portion of at least one of the button engagement structures protrudes outside the handle portion in at least one of the first and second locking positions.

16. A surgical knife safety handle according to claim 12, wherein in said first locking position, said blade is exposed.

17. A surgical knife safety handle according to claim 12, wherein in said second locking position, said blade is at least partially covered.

18. A surgical knife safety handle, comprising:
a handle portion defining a chamber therein and having a longitudinal slot, the slot accessing the chamber, the handle portion comprising first engagement structures respectively disposed adjacent to proximal and distal ends of the slot on an exterior of the handle portion, the first engagement structures comprising respective pairs of first engagement structures disposed on opposing transverse sides of the slot and defining first and second locking positions; and
a pusher for longitudinally moving a blade with respect to the handle portion, the pusher comprising:
a user control mechanism for allowing a user to longitudinally translate at least a portion of the pusher to selectively expose or at least partially cover the blade, the user control mechanism comprising:
a button disposed on the pusher and extending through the slot, the button being depressible relative to the handle portion and having a user contact portion that is narrower than the slot in a transverse direction of the slot; and
second engagement structures disposed laterally on the button for engagement with the first engagement structures to substantially secure the pusher in the first locking position in which the blade is fully extended and the second locking position in which the blade is at least partially covered;
wherein longitudinal translation of the pusher is permitted only between the first and second locking positions when the button is disposed in the slot; and
wherein a distal-most portion of the slot extends distally beyond the first engagement structures that are disposed adjacent to the distal end of the slot, and a proximal-most portion of the slot extends proximally beyond the first engagement structures that are disposed adjacent to the proximal end of the slot.

* * * * *